United States Patent
Jenkins et al.

(10) Patent No.: US 6,887,866 B2
(45) Date of Patent: May 3, 2005

(54) SHORT-ACTING SEDATIVE HYPNOTIC AGENTS FOR ANESTHESIA AND SEDATION

(75) Inventors: Thomas E. Jenkins, La Honda, CA (US); Sabine Axt, Sunnyvale, CA (US); Jennifer Bolton, San Francisco, CA (US)

(73) Assignee: Theravance, Inc., South San Francisco, CA (US)

(*) Notice: Subject to any disclaimer, the term of this patent is extended or adjusted under 35 U.S.C. 154(b) by 20 days.

(21) Appl. No.: 10/350,624

(22) Filed: Jan. 24, 2003

(65) Prior Publication Data

US 2003/0153554 A1 Aug. 14, 2003

Related U.S. Application Data

(60) Provisional application No. 60/351,385, filed on Jan. 25, 2002, and provisional application No. 60/379,219, filed on May 9, 2002.

(51) Int. Cl.[7] .................. A01N 43/00; A01N 43/40; A01N 43/36; A61K 31/55; A61K 31/44
(52) U.S. Cl. ............... 514/217.11; 514/354; 514/423; 514/534; 540/607; 546/226; 548/540; 560/37
(58) Field of Search ................. 514/217.11, 354, 514/423, 534; 546/226; 540/607; 548/540; 560/37, 75

(56) References Cited

U.S. PATENT DOCUMENTS

| | | | |
|---|---|---|---|
| 3,086,976 A | 4/1963 | Hiltman et al. | |
| 3,484,527 A | 12/1969 | Arnold et al. | |
| 3,510,559 A | 5/1970 | Arnold et al. | |
| 3,511,877 A | 5/1970 | Arnold et al. | |
| 4,401,830 A | 8/1983 | Umumura et al. | |
| 4,711,902 A | 12/1987 | Serno | |
| 4,918,092 A | * 4/1990 | Frenette et al. | 514/382 |
| 5,242,944 A | * 9/1993 | Park et al. | 514/466 |

FOREIGN PATENT DOCUMENTS

| | | |
|---|---|---|
| DE | 1134 981 | 8/1962 |
| DE | 27 31 460 A1 | 1/1978 |
| EP | 0 236 280 B1 | 6/1991 |
| GB | 1032872 | 6/1956 |
| GB | 941694 | 11/1963 |
| GB | 961 265 | 6/1964 |
| GB | 1 571 395 | 7/1980 |
| WO | WO 96/32135 | 10/1996 |

OTHER PUBLICATIONS

"SUBLIMAZE ® 2ml injection, 10ml injection" 4 pages. South African Electronic Package Inserts. Published by Malahyde Information Systems. Publication date Apr. 19, 1984, Jan. 21, 1983.*

Strazzolini et al, "Nitrolysis of t-Butyl and 1-Adamantyl Esters" Tetrahedron Letters, vol. 39, pp. 9255–9258 (1998).*

Clarke, "The Eugends", Intravenous Anaesthesia, Chapter 8, pp 162–192 (1974).

MacKenzie et al., "Formulation and evaluation of a propanidid hydroxypropryl-β-cyclodextrin solution for intravenous anesthesia", Int. Journ. of Pharmaceutics. vol. 59, pp 191–196 (1997).

Swerdlow, "A Trial of Propanidid (FBA. 1420): A New Ultrashort–Acting Anaesthetic", Brit J. Anaesth. vol. 37, pp 785–789 (1985).

Wynands et al., "A Clinical Study of Propanidid (FBA 1420)", Can. Anaes. Soc. J., vol. 12, No. 6, pp 587–594 (1985).

Zipf et al., "Local and endoanesthetic side effects of the short–term narcotic, propanidid and some homologs. Effects of a solubilizer on the degree of activity", Arzneim.–Forsch . . . vol. 17, No. 8, pp 1021–1026 (1967) (In German with English abstract).

* cited by examiner

*Primary Examiner*—Mukund J. Shah
*Assistant Examiner*—Zachary C. Tucker
(74) *Attorney, Agent, or Firm*—Robert P. Saxon; Jeffrey A. Hagenah; David E. Boone

(57) ABSTRACT

The invention provides compounds compositions and methods useful for inducing or maintaining general anesthesia or sedation in mammals.

33 Claims, 1 Drawing Sheet

SHORT-ACTING SEDATIVE HYPNOTIC AGENTS FOR ANESTHESIA AND SEDATION

CROSS REFERENCE TO RELATED APPLICATIONS

This application claims the benefit of U.S. Provisional Application Nos. 60/351,385, filed Jan. 25, 2002, and 60/379,219, filed May 9, 2002, the disclosures of which are incorporated herein by reference.

BACKGROUND OF THE INVENTION

1. Field of the Invention

This invention is directed to novel substituted phenylacetic acid ester compounds which are useful as short-acting sedative hypnotic agents for anesthesia and sedation. This invention is also directed to pharmaceutical compositions comprising such compounds; methods for using such compounds for inducing or maintaining anesthesia or sedation; and intermediates for preparing such compounds.

2. State of the Art

Propofol, 2,6-diisopropylphenol, (Diprivan® Injectable Emulsion, AstraZeneca) is an injectable anesthetic that has hypnotic properties. It can be used to induce and maintain general anesthesia and for sedation. Although propofol is a widely-used anesthetic, its usefulness is somewhat limited due to its long and unpredictable post infusion duration of action. This unpredictable duration of action leads to irregular and often long patient recovery times that are undesirable.

Propanidid [4-[(N,N-diethylcarbamoyl)methoxy]-3-methoxyphenyl]acetic acid propyl ester), is another injectable anesthetic that has been approved for use in several countries outside the United States. Although propanidid provides a much shorter and predictable recovery time than propofol, it is not as potent an anesthetic. Additionally, Epontol®, an injectable emulsion formulation of propanidid, provided by Bayer, was withdrawn from the market in Great Britain in 1983 because of concern over anaphylactoid reactions. Thus, in spite of the fact that propanidid provides shorter and more predictable recovery times than propofol, it has not been accepted widely as an injectable anesthetic.

Currently there is a need for novel injectable anesthetic agents. Preferred agents will have a shorter and more predictable duration of action than propofol. Preferred agents will also be more potent than propanidid.

SUMMARY OF THE INVENTION

Applicants have discovered novel substituted phenylacetic acid ester compounds which are useful as short-acting sedative hypnotic agents. The agents have a shorter and more predictable duration of action than propofol and are also more potent than propanidid.

Accordingly, this invention provides a compound of formula (I):

wherein:

$R^1$ is selected from the group consisting of $(C_2-C_6)$alkyl, $(C_2-C_6)$alkenyl, $(C_2-C_6)$alkynyl, $(C_3-C_6)$cycloalkyl $(C_1-C_6)$alkyl, phenyl, and benzyl;

$R^2$ and $R^3$ are each independently selected from the group consisting of $(C_1-C_6)$alkyl, $(C_2-C_6)$alkenyl, and $(C_2-C_6)$alkynyl, or $R^2$ and $R^3$, together with the nitrogen atom to which they are attached, form a heterocyclic ring having from 5 to 7 atoms; and $R^4$ is selected from the group consisting of $(C_1-C_6)$alkyl, $(C_2-C_6)$alkenyl, and $(C_2-C_6)$alkynyl;

provided that the sum of the carbon atoms in $R^1$, $R^2$, $R^3$, and $R^4$ is greater than 7.

The invention is also directed to intermediates useful for preparing compounds of formula (I). Accordingly, the invention provides a compound of formula (II):

wherein $R^1$ and $R^4$ are as defined herein and $R^5$ is hydrogen or hydroxyl.

The invention further provides a pharmaceutical composition comprising a pharmaceutically acceptable carrier and a therapeutically effective amount of a compound of formula (I).

The compounds of the invention are highly effective short-acting sedative hypnotic agents for use in the induction and maintenance of anesthesia and sedation. Accordingly, the invention also provides a method for inducing or maintaining anesthesia or sedation in a mammal, comprising administering to the mammal an effective amount of a compound of the invention. The invention also provides a method for inducing or maintaining anesthesia or sedation in a mammal, comprising administering to the mammal an effective amount of a pharmaceutical composition of the invention.

DETAILED DESCRIPTION OF THE INVENTION

When describing the compounds, compositions and methods of the invention, the following terms have the following meanings, unless otherwise indicated.

The term "$(C_1-C_6)$alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, n-hexyl, and the like. As used herein, "Me" represents methyl, "Et" represents ethyl, "propyl" and "Pr" represent n-propyl, and "iPr" represents iso-propyl.

The term "$(C_2-C_6)$alkenyl" refers to a monoradical of a branched or unbranched unsaturated hydrocarbon group having from 2 to 6 carbon atoms and having at least 1 site of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "$(C_2-C_6)$alkynyl" refers to a monoradical of an unsaturated hydrocarbon having from 2 to 6 carbon atoms and having at least 1 triple bond. Preferred alkynyl groups include ethynyl (—C≡CH), propargyl (—CH$_2$C≡CH) and the like.

The term "$(C_3-C_6)$cycloalkyl" refers to cyclic alkyl groups of from 3 to 6 carbon atoms having a single cyclic ring. Such cycloalkyl groups include, by way of example, single ring structures such as cyclopropyl, cyclobutyl, cyclopentyl, cyclohexyl and the like.

The term "$(C_3-C_6)$cycloalkyl$(C_1-C_6)$alkyl" refers to a group of the formula $(C_3-C_6)$cycloalkyl$(C_1-C_6)$alkyl-, wherein $(C_3-C_6)$cycloalkyl and $(C_1-C_6)$alkyl are as defined above.

The compounds of this invention can contain one or more chiral centers. Accordingly, this invention is intended to include racemic mixtures, diastereomers, enantiomers and mixtures enriched in one or more stereoisomer. The scope of the invention as described and claimed encompasses the racemic forms of the compounds as well as the individual enantiomers and non-racemic mixtures thereof.

The term "hypnotic agent" refers generally to a compound that promotes sleep. As used in pharmacology, the term "hypnotic agents" describe agents used to induce or maintain anesthesia, sedation, or sleep.

The term "anesthesia" as used herein refers to a loss of sensation or awareness resulting from pharmacologic depression of nerve function.

The term "sedation" is defined herein as the calming of mental excitement or abatement of physiological function by administration of a drug.

The term "effective amount" refers to that amount which is sufficient to induce or maintain anesthesia or sedation when administered to a mammal. The effective amount will vary depending on the subject and the manner of administration, and may be determined routinely by one of ordinary skill in the art.

The term "analgesic" refers to a compound that relieves pain by altering perception of nociceptive stimuli without producing significant anesthesia or loss of consciousness.

The term "opioid" refers to synthetic narcotics that have opiate-like activities (e.g., analgesia), but are not derived from opium.

The term "short-acting" as used herein refers to agents that are pharmacokinetically responsive. When short-acting agents are administered by infusion, the effects of the agents cease promptly upon termination of the infusion.

While a broad definition of the invention is set forth in the Summary of the Invention, certain agents or compositions may be preferred. Specific and preferred values listed herein for radicals, substituents, and ranges are for illustration only; they do not exclude other defined values or other values within defined ranges for the radicals and substituents.

A preferred agent that can be incorporated into the compositions of the invention and that can be administered according to the methods of the invention is a compound of formula (I) as described above, wherein the sum of the number of carbon atoms in $R^1$, $R^2$, $R^3$, and $R^4$ ranges from 8 to 15.

More preferably, the sum of the number of carbon atoms in $R^1$, $R^2$, $R^3$, and $R^4$ ranges from 8 to 12.

Preferably, $R^1$ is selected from the group consisting of $(C_2-C_6)$alkyl, $(C_2-C_6)$alkenyl, and $(C_2-C_6)$alkynyl.

In another preferred embodiment, $R^1$ is selected from the group consisting of $(C_3-C_6)$cycloalkyl, phenyl, and benzyl.

In another more preferred embodiment, $R^1$ is selected from the group consisting of $(C_2-C_4)$alkyl, $(C_2-C_4)$alkenyl, and $(C_2-C_4)$alkynyl.

In another more preferred embodiment, $R^1$ is selected from the group consisting of $(C_2-C_4)$alkyl, cyclopropyl, and cyclobutyl.

Even more preferably, $R^1$ is $(C_2-C_4)$alkyl.

Most preferably, $R^1$ is ethyl or propyl.

Preferably, $R^2$ is selected from the group consisting of $(C_1-C_4)$alkyl, $(C_2-C_4)$alkenyl, and $(C_2-C_4)$alkynyl.

In an alternative preferred embodiment, $R^2$ and $R^3$ together with the nitrogen atom to which they are attached form a piperidinyl ring.

More preferably, $R^2$ is $(C_1-C_4)$alkyl.

Preferably, $R^3$ is selected from the group consisting of $(C_1-C_4)$alkyl, $(C_2-C_4)$alkenyl, and $(C_2-C_4)$alkynyl.

More preferably, $R^3$ is $(C_1-C_4)$alkyl.

Preferably, $R^4$ is selected from the group consisting of $(C_1-C_4)$alkyl, $(C_2-C_4)$alkenyl, and $(C_2-C_4)$alkynyl.

More preferably, $R^4$ is $(C_1-C_4)$alkyl.

In a preferred embodiment, $R^1$ is $(C_2-C_4)$alkyl; $R^2$ and $R^3$ are each independently $(C_1-C_4)$alkyl; and $R^4$ is $(C_1-C_4)$ alkyl.

A preferred sub-group of compounds is that in which $R^1$ is $(C_2-C_4)$alkyl; $R^2$ and $R^3$ are each independently $(C_1-C_4)$ alkyl; $R^4$ is $(C_1-C_4)$alkyl; and the sum of the number of carbon atoms in $R^1$, $R^2$, $R^3$, and $R^4$ ranges from 8 to 12.

Within this sub-group, preferably $R^1$ is ethyl or propyl; $R^2$, $R^3$, and $R^4$ are each independently selected from the group consisting of methyl, ethyl, and propyl; and the sum of the number of carbon atoms in $R^1$, $R^2$, $R^3$, and $R^4$ ranges from 8 to 11. Particular preferred values for the sum of the number of carbon atoms are 9, 10, and 11.

Preferred compounds of the invention are compounds of formula (I) in which $R^1$, $R^2$, $R^4$ represent the values shown in Table I below.

TABLE I

| Compound | R¹ | R² | R³ | R⁴ |
|---|---|---|---|---|
| 1 | Et | Et | Et | Pr |
| 2 | Et | Et | Et | Et |
| 3 | Et | Et | Et | iPr |
| 4 | Pr | Et | Et | Pr |
| 5 | Et | Pr | Pr | Et |
| 6 | Et | Pr | Pr | Pr |
| 7 | Et | Me | Et | Pr |
| 8 | Et | Et | Pr | Et |
| 9 | Et | Et | Pr | Pr |
| 10 | Pr | Me | Me | Pr |
| 11 | Pr | Et | Pr | Pr |
| 12 | Pr | Pr | Pr | Pr |
| 13 | Pr | Me | Et | Pr |
| 14 | Pr | Et | Pr | Et |

Particularly preferred are compounds in which $R^1$ is ethyl or propyl, $R^2$ and $R^3$ each ethyl, and $R^4$ is propyl. Compound 1 is most particularly preferred.

General Synthetic Procedures

The intermediates and compounds of this invention can be prepared from readily available starting materials using known synthetic procedures. For example, the compounds can be prepared as outlined generally below and further described in the Examples. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, Protecting Groups in Organic Synthesis, Third Edition, Wiley, New York, 1999, and references cited therein.

The present synthetic methods make use of novel intermediates of formula (II), specifically (IIa) or (IIb):

(IIa)

(IIb)

In a first method of synthesis, compounds of formula (I) are prepared by alkylating a compound of formula (IIa) with the requisite compound of formula $X-CH_2C(=O)NR^2R^3$, wherein X is a suitable leaving group (e.g. chloro, bromo, tosyl, or mesyl.)

In a second method of synthesis, compounds of formula (IIb) are alkylated with the requisite acetamide compounds of formula $X-CH_2C(=O)NR^2R^3$ to produce a compound of formula (III):

(III)

which is reduced to form a compound of formula (I). As exemplified in Examples 4A, 4B, and 10–13, a useful method of reduction proceeds by a two-step reaction in which the hydroxyl of formula (III) is first acetylated, before reaction with hydrogen.

The intermediate of formula (IIb) used in the above procedure is prepared from commercially available starting materials and reagents using conventional procedures. For example, the intermediate can be prepared as shown in Scheme A:

Scheme A

As illustrated above, catechol is coupled with a compound of formula $R^1X$, where X is a leaving group, to form the ether (IV) which is reacted with glyoxylic acid to produce compound (V). Subsequent reaction of (V) with an excess of the alcohol $R^4OH$ provides the intermediate of formula (IIb). The intermediate (IIb) can be alkylated as described above to produce a compound of formula (III).

The intermediate of formula (Ia) can be prepared, for example, as described in Example 1 sub-part (1) and also as illustrated in Scheme B in Example 1 sub-part (2) below.

Pharmaceutical Compositions

The compounds of formula I can be formulated as pharmaceutical compositions and administered to a mammalian host, such as an animal or a human patient, in a variety of forms adapted to the chosen route of administration, i.e., orally or parenterally, by intravenous, intramuscular, topical or subcutaneous routes.

Thus, the present compounds can be systemically administered, e.g., orally, in combination with a pharmaceutically acceptable vehicle such as an inert diluent or an edible carrier. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations can, of course, be varied and can conveniently be between about 2 to about 60% of the weight of a given unit dosage form. The amount of active compound in such therapeutically useful compositions is such that an effective dosage level will be obtained.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Active agents described herein are typically formulated as pharmaceutical compositions which are suitable for intravenous administration. The present active agents are relatively insoluble in water. Thus, for intravenous administration, the agents are typically formulated in aqueous media using one or more water-immiscible solvent and one or more emulsifier. Some emulsifiers are variously termed surfactants in the literature. Individual formulations can include one or more additional components such as stabilizers, tonicity modifiers, bases or acids to adjust pH, and solubilizers. The formulations can also optionally contain a preservative, such as ethylenediaminetetraacetic acid (EDTA) or sodium metabisulfite, to name only a few.

A wide range of water-immiscible solvents can be used in the compositions of the present invention. The water-immiscible solvent can be a vegetable oil, for example soybean, safflower, cottonseed, corn, sunflower, arachis, castor or olive oil. Alternatively, the water-immiscible solvent is an ester of a medium or long-chain fatty acid, for example, a mono-, di-, or triglyceride; an ester of a combination of a medium and long-chain fatty acid, or is a chemically modified or manufactured material such as ethyl oleate, isopropyl myristate, isopropyl palmitate, a glycerol ester, polyoxyl, or hydrogenated castor oil. The water-immiscible solvent can also be a marine oil, for example cod liver or another fish-derived oil. Suitable solvents also include fractionated oils, for example, fractionated coconut oil or modified soy bean oil.

The compositions can also comprise an emulsifier. Suitable emulsifiers include synthetic non-ionic emulsifiers, for example ethoxylated ethers and esters and polyoxypropylene-polyoxyethylene block co-polymers, and phospholipids. Both naturally-occurring phospholipids, such as egg and soya phospholipids, and modified or artificially manipulated phospholipids, for example prepared by physical fractionation and/or chromatography, or mixtures thereof can be used. Phospholipids are alternatively termed phosphatides. Preferred emulsifiers are egg phospholipids and soya phospholipids. Egg yolk phospholipids are principally composed of phosphatidylcholine and phosphatidylethanolamine. Lecithin, which is classified as a phosphatidylcholine, and which can be derived from egg yolk or soybeans, is another commonly used emulsifier.

The pharmaceutical formulations can also include stabilizing agents, which can alternatively be considered as co-emulsifiers. Anionic stabilizers include phosphatidylethanolamines, conjugated with polyethylene glycol, (PEG-PE) and phosphatidylglycerols, a specific example of which is dimyristolphosphatidylgylcerol (DMPG). Additional examples of useful stabilizers include oleic acid and its sodium salt, cholic acid and deoxycholic acid and their respective salts, cationic lipids such as stearylamine and oleylamine, and 3β-[N-(N',N'-dimethylaminoethane)carbamoyl]cholesterol (DC-Chol).

The pharmaceutical compositions of the invention can be made isotonic with blood by the incorporation of a suitable tonicity modifier. Glycerol is most frequently used as a tonicity modifier. Alternative tonicity modifying agents include xylitol, mannitol, and sorbitol. The pharmaceutical compositions are typically formulated to be at physiologically neutral pH, typically in the range 6.0–8.5. The pH can be adjusted by the addition of base, for example NaOH or NaHCO$_3$, or in some cases acid, such as HCl.

Pharmaceutically safe oil-water emulsions comprising a vegetable oil, a phosphatide emulsifier, typically egg lecithin or soybean lecithin, and a tonicity modifier are provided commercially for parenteral nutrition, for example, under the tradenames Liposyn® II and Liposyn® III (Abbott Laboratories, North Chicago, Ill.) and Intralipid® (Fresenius Kabi AB, Uppsala, Sweden.) The agents described herein can be formulated with these or other similar oil-water emulsions, as shown, for example, in injections 5 through 9 of Example 16 below.

A compound of the invention can also be formulated in a triglyceride comprising esters of at least one medium chain length ($C_6$–$C_{12}$) fatty acid. Preferably the triglyceride comprises an ester of a $C_8$–$C_{10}$ fatty acid. Triglycerides suitable for formulating a compound of the invention are provided under the tradename Miglyol® by Condea Chemie GmbH (Witten, Germany.). For example, Miglyol® 810 or 812 (caprylic ($C_{10}$)/capric ($C_8$) glyceride)are useful for formulation of the present agents. Injection 11 of Example 16 below shows a formulation including egg yolk phosphatides as the emulsifier, DMPG as an anionic stabilizer, and glycerol as the tonicity modifier, in which Miglyol® 810 is used as the oil phase.

Additionally, the agents described herein can be formulated analogously to pharmaceutical compositions of propanidid known to the art. For example, compounds of the invention can be formulated in mixtures including an ester of a medium chain length fatty acid, as discussed in U.S. Pat. No. 4,711,902. Furthermore, the compounds described herein can be formulated analogously to compositions of propofol known to the art as described, for example, in U.S. Pat. Nos. 4,056,635; 4,452,817; and 4,798,846.

In yet another alternative, the present compounds can be formulated using a solubilizer, for example, hydroxypropyl-β-cyclodextrin, to form an inclusion complex.

Still other suitable formulations for use in the present invention can be found in Remington's Pharmaceutical Sciences, Mace Publishing Company, Philadelphia, Pa., 17th ed. (1985).

Compounds according to the present invention are potent hypnotic agents which are metabolized rapidly in vivo to an inactive and well-tolerated carboxylic acid metabolite (Formula I where $R^4$ is hydrogen.) The present compounds exhibit one or more of the following beneficial properties as compared with previous agents: increased potency, shorter recover times, reduced cardiovascular effects, lower toxicity, and higher therapeutic index, where therapeutic index is defined as the ratio of maximum tolerated dose to effective dose.

Thus, compounds of the present invention can be used for the induction and/or maintenance of general anesthesia, for the initiation and/or maintenance of conscious sedation with patients spontaneously breathing, and for the induction and/or maintenance of sedation for intubated, mechanically ventilated patients.

The amount of an active agent required for use in the methods of the invention will vary with the route of administration, the age and condition of the patient, and the degree of anesthesia or sedation required, and will be ultimately at the discretion of the attendant physician or clinician.

In general, the agents can be administered as an initial bolus dose to produce anesthesia or sedation, followed by a continuous infusion of agent at a rate that is sufficient to achieve and maintain the level of anesthesia or sedation desired. Alternatively, a continuous infusion of an agent of the present invention can be used to maintain anesthesia or sedation following induction or induction and maintenance with another sedative hypnotic agent, (e.g. propofol, a barbiturate, such as nembutal® (pentobarbital sodium) or brevital® sodium (methohexital sodium), or a benzodiazepine, such as valium®).

For example, a suitable bolus dose of the present agent for a human patient will typically be in the range of from about 0.1 to about 50 milligrams/kilogram (mg/kg), preferably about 0.5 to about 20 mg/kg. The rate of infusion will typically be in the range from about 5 to about 5000 micrograms/kilogram/minute (μg/kg/min), preferably about 10 to about 2000 μg/kg/min.

The compounds of the invention can also be administered in combination with other therapeutic agents, such as, for example, other sedative hypnotic agents, analgesics (e.g. an opioid such as the μ-opioid agonist remifentanil, fentanyl, sulfentanil, or alfentanil), or paralytic agents, such as atracurium besylate or pancuronium bromide. Accordingly, the compositions of the invention can optionally further comprise another therapeutic agent, for example, a sedative hypnotic agent, analgesic, or paralytic agent. Similarly, the therapeutic methods of the invention can also optionally comprise administering another therapeutic agent (e.g. a sedative hypnotic agent, analgesic, or paralytic agent) to the mammal.

The ability of an agent to function as an anesthetic or a sedative can be determined using assays that are known in the art (for example see U.S. Pat. No. 5,908,869, or R. James and J. Glen, *J. Med Chem.*, 23, 1350 (1980)) or using the assay described in Test A, below.

Test A

Methods

Formulation

Test compounds, e.g., representative compounds of the invention as well as the comparison compound, propanidid, were formulated in (1) 10% cremophor EL/90% D5W (5% dextrose in distilled water;) (2) 10% Liposyn® III (Intravenous Fat Emulsion, containing (per 100 mL) 10 g soybean oil, 1.2 g egg phosphatides and 25 g glycerol), available from Abbott Laboratories, North Chicago, Ill.; and (3) injections (10) or (11) (as described in Example 16) with Miglyol® 810 (caprylic/capric glyceride). Typically, formulation (1) above was used for bolus dosing and formulations (2) or (3) for infusion dosing. Compounds of the invention and propanidid were synthesized as described in Examples 1–15 below. Propofol formulated in soybean oil, sold as Diprivan® injectable emulsion was obtained from AstraZeneca (Wilmington, Del.).

Bolus Administration (Rats)

Rats (adult male Sprague-Dawley) were placed in a perspex restrainer and injected (1 or 2 mL/kg over approximately 3 seconds) with the compound of interest via the tail vein. The time to onset of anesthesia (defined as a loss of righting reflex), duration of anesthesia (i.e. duration of loss of righting reflex) and behavioral recovery (i.e. duration of ataxia, sedation and/or lethargy following the return of the righting reflex) was recorded. Duration of anesthesia was measured by placing the rats on their backs following onset of anesthesia and the time until recovery of the righting reflex was recorded using a stop clock. The depth of anesthesia was assessed intermittently by observing the magnitude of the withdrawal reflex to noxious pinch of the hind paw. Behavioral recovery was assessed by visual observation.

Bolus Administration (Guinea Pigs)

Adult male guinea pigs were dosed by bolus administration (0.1–0.25 mL volume) via an ear vein. Duration of loss of righting reflex was measured as described above for rats.

Administration by Infusion (Rats)

Rats (adult Sprague-Dawley) were placed in a perspex restrainer and anesthesia induced by bolus injection via the tail vein (0.15–1 mL/kg over approximately 3 seconds at a dose, estimated from the earlier bolus experiments, to produce anesthesia of approximately 2 minutes duration). Immediately after bolus administration, an infusion (with a duration of typically 20, 180 or 300 minutes), via the tail vein, was commenced (0.075–0.5 mL/kg/min at a half of the bolus dose/min). In some experiments, the initial infusion rate was maintained throughout, while in others, the rate was modified as necessary to maintain a consistent depth of anesthesia (as defined by moderate paw withdrawal in response to noxious pinch). Following completion of the infusion, duration of anesthesia (i.e. duration of loss of righting reflex) and behavioral recovery (i.e. duration of ataxia, sedation or lethargy following return of the righting reflex) was recorded.

Results

Figure 1:
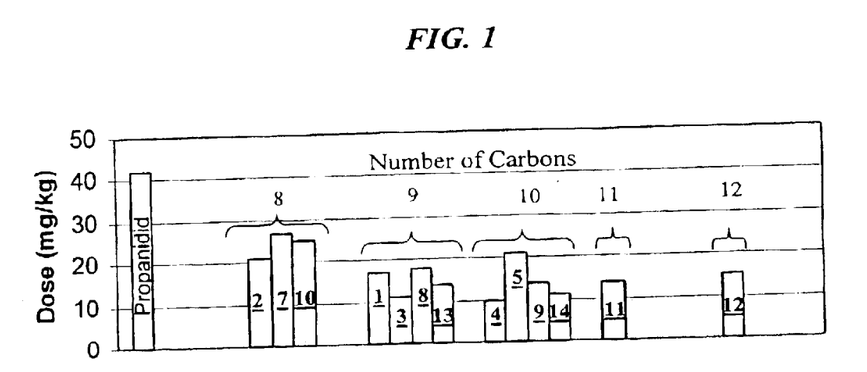
FIG. 1 compares the dose in mg/kg of compounds of the invention to produce a mean loss of righting reflex of 2 minutes in rats with the dose required of the prior art compound, propanidid.

Bolus administration (rats): The dose response curve for duration of loss of righting reflex in rats resulting from bolus injection of test compounds prepared in formulation (1) was determined. To quantify anesthetic potency, the doses of test compound which produced a mean loss of righting reflex of 2 minutes was calculated. FIG. 1 compares the bolus dose of compounds of the invention in mg/kg producing 2 minutes of loss of righting reflex with the required dose of the comparison compound, propanidid.

Bolus administration (guinea pigs): The potency of compound 1 was also tested in guinea pigs by the analogous procedure. The dose of compound 1 required to produce 2 minutes of loss of righting reflex in guinea pigs was calculated to be 8 mg/kg, as compared with a dose of 13 mg/kg for propanidid.

Administration by infusion (rats): Recovery times following termination of administration by infusion in rats were determined for compound 1 and for the comparison compounds propofol and propanidid. The duration of the loss of righting reflex (in minutes) following termination of infusion is given as a function of duration of infusion in Table 2 below.

TABLE 2

Duration of Loss of Righting Reflex in Minutes Following Termination of Infusion

| | 20 minute Infusion | 3 hour Infusion | 5 hour Infusion |
|---|---|---|---|
| Propofol | 30.0 ± 2.9 | 47.8 ± 5.3 | 59.0 ± 1.4 |
| Compound 1 | 1.4 ± 0.1 | 1.7 ± 0.1 | 2.6 ± 1.0 |
| Propanidid | 1.6 ± 0.2 | 1.4 ± 0.1 | |

Figure 2:
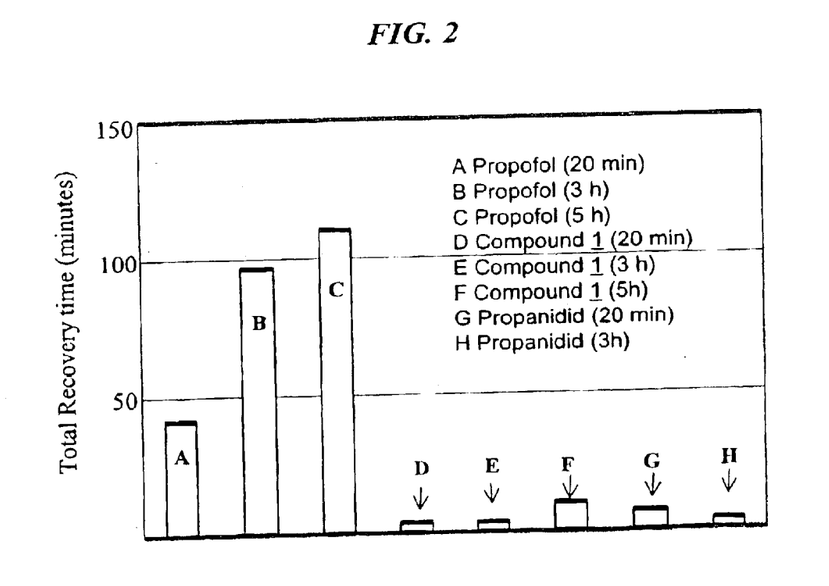
FIG. 2 compares the total recovery time in minutes following termination of infusions of 20 minutes, 3 hours, and 5 hours in rats of compound 1 of the present invention with the recovery time following termination of infusion of the prior art compounds propanidid and propofol.

FIG. 2 shows total recovery times in minutes following termination of infusion of specified duration in rats, as the sum of the duration of the loss of righting reflex, as given in Table 2, and the duration of behavioral recovery after the return of the righting reflux.

As demonstrated by the above data in the rat and guinea pig animal models, compounds of the invention tested are more potent general anesthetics than propanidid, and provide significantly shorter total recovery rates than propofol, even after long (5 hour) infusions. In addition, the duration of loss of righting reflex following termination of infusion for the tested compound of the invention was independent of the duration of infusion within the uncertainty of the experimental results.

The in vitro stability of representative compounds of the invention can be determined as described in Test B.

Test B

Source of Whole Blood Samples

Rat and guinea pig whole blood samples, obtained by cardiac puncture, were collected in vacutainer tubes containing sodium heparin. The samples were kept in ice and used the same day of collection. Dog, monkey and human whole blood, purchased from commercial vendors, was maintained on wet ice and used the day following collection.

Metabolism Assay

The test compounds, propanidid and a representative compound of the invention, were spiked into 300 $\mu$L of a whole blood sample to a final concentration of 100 $\mu$M. The proteins were immediately precipitated with the addition of twice the volume of ice-cold ethanol and vortex mixing. This constituted the zero time point. In identical 300 $\mu$L incubations, spiked whole blood samples were then incubated at 37° C. for 30 seconds to 60 minutes. At a predetermined time point, 600 $\mu$L of ice-cold ethanol was added to the mixture to terminate the incubation. Following termination of the incubation, the samples were centrifuged and the supernatants dried under a stream of nitrogen at room temperature. The residue was reconstituted in 150 $\mu$L of sterile water and then centrifuged. An aliquot (50 $\mu$L) of the supernatant was injected to HPLC-UV for analysis.

HPLC Method

A $C_{18}$, 5 $\mu$m, 2×150 mm I.D (LUNA, Phenomenex) reverse-phase HPLC column was used and a gradient from 10% to 68% acetonitrile over 15 minutes followed by a 5 minute isocratic run at 10% acetonitrile was used. The mobile phase components contained 0.1% TFA. The analytes were monitored by UV detection at 214 nm.

Data Analysis

Concentrations of the substrate in incubates were measured as peak area ratios using the internal standard method and percent degradation was measured relative to the zero time values.

Results

The tested compounds of formula (I) were metabolized rapidly to the corresponding carboxylic acids (formula (I) wherein $R^4$=hydrogen). The acid metabolites were found to be inactive as anesthetics in Test A. The rapid conversion of the compounds of formula (I) to their acid metabolites, and the inactivity of these acid metabolites as anesthetics, may be at least partially responsible for the shorter and more predictable recovery rates observed for the compounds of formula (I).

The invention will now be illustrated by the following non-limiting Examples.

EXAMPLES

In the examples below, the following abbreviations have the following meanings. Any abbreviations not defined have their generally accepted meaning. Unless otherwise stated, all temperatures are in degrees Celsius.

| | |
|---|---|
| DMSO = | dimethyl sulfoxide |
| EtOAc = | ethyl acetate |
| DCM = | dichloro methane |
| PPTS = | pyridinium para-toluene sulphonate |
| DMF = | dimethyl formamide |

General: Unless noted otherwise, reagents, starting material and solvents were purchased from commercial suppliers, for example Sigma-Aldrich (St. Louis, Mont.) and Trans World Chemicals, Inc. (TCI) (Rockville, Md.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by vacuum distillation; NMR samples were dissolved in deuterated solvent ($CD_3OD$, $CDCl_3$, or DMSO-d6), and spectra were acquired with a Varian Gemini 2000 instrument (300 MHz) using the listed solvent as the internal standard unless otherwise indicated; and mass spectrometric identification was performed by an electrospray ionization method (ESMS) with a Perkin Elmer instrument (PE SCIEX API 150 EX).

Example 1

Compound 1: [4-[(N,N-Diethylcarbamoyl)methoxy]-3-ethoxyphenyl]acetic acid propyl ester In a 50 mL round bottom flask equipped with a magnetic stir bar, 3-ethoxy-4-hydroxyphenylacetic acid propyl ester (800 mg, 3.4 mmol, 1.0 equiv.) was dissolved in dry acetone (20 mL). To the solution was added $K_2CO_3$ (705 mg, 5.1 mmol, 1.5 equiv.) followed by 2-chloro-N,N-diethylacetamide (0.55 mL, 4.0 mmol, 1.2 equiv., available from Aldrich). Under vigorous stirring, the suspension was warmed to reflux and kept under those conditions for 15 hours. After cooling to room temperature the reaction mixture was filtered through a folded paper filter and the remaining solution freed of solvent under reduced pressure. The oily product was purified by column chromatography ($SiO_2$, 50% EtOAc/hexane) to yield 630 mg (53% of theory) of colorless oil which was 99.6% pure by HPLC.

TLC (silica, 50% EtOAc/hexane) Rf 0.25; $^1H$ NMR ($CDCl_3$, 300 MHz) d 0.90 (3H, t, propylate $CH_3$), 1.13 and 1.20 (each 3H, t, N-ethyl $CH_3$), 1.43 (3H, t, ethoxy $CH_3$), 1.60–1.67 (2H, m, propylate $CH_2$), 3.35–3.46 (4H, m, N-ethyl $CH_2$), 3.53 (2H, s, $OCH_2CO$), 4.01–4.11 (4H, m, 2×$OCH_2$), 4.70 (2H, s, $ArCH_2CO$), 6.75–6.91 (3H, m, ArH). m/z: $[M+H^+]$ calcd for $C_{19}H_{29}NO_5$ 352.22; found 352.

(1) Preparation of the Intermediate of Formula (IIa) $R^1$=ethyl and $R^4$=propyl (3-ethoxy-4-hydroxyphenylacetic Acid Propyl Ester)

A 30 mL glass pressure tube with teflon screwcap was equipped with a magnetic stir bar and filled with 3-ethoxy-4-hydroxyphenylacetic acid (2.5 g, 12.7 mmol, 1.0 equiv., available from Trans World Chemicals). 1-Propanol (20 mL, 270 mmol, ~20 equiv.) was added and the mixture stirred to dissolve. Concentrated sulfuric acid (2 drops) was added. The tube cap was screwed down hand tight and the tube was immersed into an oil bath. The reaction was allowed to stir at 90° C. for 15 hours. The tube was allowed to cool to room temperature after which the contents were transferred to a round bottom flask and the excess alcohol distilled off in vacuo. The remaining oil was taken up in ethyl acetate (50 mL) and washed with saturated sodium bicarbonate solution. After drying over magnesium sulfate and filtration the solvent was distilled off under reduced pressure to leave 2.6 g (85% yield) of the ester as a light yellow oil.

(2) Preparation of the Intermediate of Formula (IIa), $R^1$=ethyl and $R^4$=propyl (3-ethoxy-4-hydroxyphenylacetic Acid Propyl Ester)

The title intermediate was also prepared according to Scheme B below

-continued (a) Preparation of Compound B1

2-Ethoxyphenol (56.6, 0.401 mol, 1 eq.), glyoxylic acid (50% aqueous solution) (41.0 mL, 0.396 mol, 0.99eq.), and distilled water (110 mL) were combined. The mixture was cooled in an ice bath, and a solution of 10% NAOH (32.2 g NaOH in 300 mL distilled water, 0.805 mol, 2 eq.) was slowly added via addition funnel. The reaction was allowed to slowly warm to room temperature, and after ~18 hours, the solution was washed with ethyl acetate (4×250 mL), then acidified with 6N HCl until pH ~3. NaCl was added and the product was then extracted into ethyl acetate (4×200 mL). The organic phase was washed with brine, dried over magnesium sulfate, and solvent was removed under vacuum, giving 51.8 g of B1 as a light pink solid.

$^1$H NMR (DMSO-$d_6$, 300 MHz): δ 1.24 (t, 3H), 3.90 (q, 2H), 4.79 (s, 1H), 5.59 (bs, 1H), 6.67 (q, 2H), 6.86 (s, 1H), 8.81 (s, 1H), 12.35 (bs, 1H).

(b) Preparation of Compound B2

Compound B1 (45.0 g, 0.212 mol, 1 eq.) was dissolved in DCM (225 mL), pyridine (80 mL, 0.989 mol, 6 eq.) was added and the mixture was cooled in an ice bath under nitrogen. Acetic anhydride (100 mL, 1.06 mol, 4 eq.) was added slowly via addition funnel. The mixture was stirred (~3 hr) until reaction was complete and then diluted with diethyl ether (500 mL) and washed with 1N HCl (4×250 mL). The mixture was extracted into 8% sodium bicarbonate solution (4×80 mL), acidified to ~pH 4 with 6N HCl, and the product extracted into diethyl ether, giving 41.1 g of B2 as a white crystalline solid.

$^1$H NMR (DMSO-$d_6$, 300 MHz): δ 1.12 (t, 3H), 2.05 (s, 3H), 2.17 (s, 3H), 3.95 (q, 2H), 5.72 (s, 1H), 6.96 (d, 1H), 7.04 (d, 1H), 7.12 (s, 1H).

(c) Preparation of Compound B3

Compound B2 (30.9 g, 0.104 mol) was dissolved in methanol (500 mL), Pd(OH)$_2$ (5.0 g) wet with distilled water was added, and the mixture was placed under hydrogen at 30 psi with shaking. After 48 hr Pd(OH)$_2$ was removed by filtration and solvent was removed under vacuum giving 22 g of B3 as a yellow oil.

$^1$H NMR (DMSO-$d_6$, 300 MHz): δ 1.19 (t, 3H), 2.16 (s, 3H), 3.47 (s, 2H), 3.92 (q, 2H), 6.74 (d, 1H), 6.91 (m, 2H).

(d) Preparation of 4-Hydroxyphenylacetic Acid Propyl Ester

Compound B3 (1.40 g, 5.87 mmol) was dissolved in an excess of 1-propanol (50 mL), concentrated H$_2$SO$_4$ (3 drops) was added, and the mixture was heated at 90° C. for ~18 hours. The volume of 1-propanol was reduced under vacuum, then the mixture was diluted with diethyl ether, washed with saturated sodium bicarbonate solution (2×), distilled water (1×), brine (1×), dried over magnesium sulfate and solvent was removed under vacuum, giving 4-hydroxyphenylacetic acid propyl ester as a yellow oil.

$^1$H NMR (DMSO-$d_6$, 300 MHz): δ 0.78 (t, 3H), 1.25 (t, 3H), 1.48 (q, 2H), 3.44 (s, 2H), 3.92 (m, 4H), 6.58 (d, 1H), 6.64 (d, 1H), 6.74 (s, 1H), 8.73 (s, 1H).

Example 2

Compound 2: [4-[(N,N-Diethylcarbamoyl)methoxy]-3-ethoxyphenyl]acetic acid ethyl ester Using a procedure similar to that described in Example 1, except replacing the 1-propanol with ethanol in the synthesis of the intermediate, to produce an intermediate of formula (IIa) with R$^1$=ethyl and R$^4$=propyl, the title compound was prepared in 81% yield as a colorless oil that was 96% pure by HPLC.

TLC (silica, 50% EtOAc/hexane) Rf 0.25; $^1$H NMR (CDCl$_3$, 300 MHz) d 1.13–1.22 (6H, m, N-ethyl CH$_3$), 1.25 (3H, t, ethyl ester CH$_3$), 1.43 (3H, t, ethoxy CH$_3$), 3.38-3.45 (4H, m, N-ethyl CH$_2$), 3.52 (2H, s, OCH$_2$CO), 4.05–4.17 (4H, m, 2×OCH$_2$), 4.71 (2H, s, ArCH$_2$CO), 6.78–6.91 (3H, m, ArH). m/z: [M+H$^+$] calcd for C$_{18}$H$_{27}$NO$_5$ 338.20; found 338.

Example 3

Compound 3: [4-[(N,N-Diethylcarbamoyl)methoxy]-3-ethoxyphenyl]acetic acid isopropyl ester Using a procedure similar to that described in Example 1, except replacing the 1-propanol with isopropanol in the synthesis of the intermediate to produce an intermediate of formula (IIa) with R$^1$=ethyl and R$^4$=isopropyl, the title compound was prepared in 63% yield as a colorless oil that was 99% pure by HPLC.

TLC (silica, 50% EtOAc/hexane) Rf 0.25; $^1$H NMR (CDCl, 300 MHz) d 1.06–1.19 (6H, m, N-ethyl CH$_3$), 1.14 and 1.16 (2×3H, 2s, isopropyl ester CH$_3$), 1.36 (3H, t, ethoxy CH$_3$), 3.30–3.36 (4H, m, N-ethyl CH$_2$), 3.42 (2H, s, OCH$_2$CO), 3.98–4.03 (2H, m, OCH$_2$), 4.64 (2H, s,

ArCH$_2$CO), 4.90–4.98 (1H, m, CH), 6.71–6.84 (3H, m, ArH). m/z: [M+H$^+$] calcd for C$_{19}$H$_{29}$NO$_5$ 352.22; found 352.

Example 4A

Compound 4: [4-[(N,N-Diethylcarbamoyl)methoxy]-3-propoxyphenyl]acetic acid propyl ester Compound 4 was prepared according to Scheme C below (1) Preparation of Compound C1 (Formula (IV) R$^1$=propyl)

A solution of catechol (81.0 g, 0.74 mol) in DMF (1.5 mL) in a 3 L flask equipped with an overhead stirrer was prepared and cooled in an ice bath. Slowly NaH (60% in oil) (29 g, 0.73 mol) was added to the solution, once it had completely reacted (about 1 hr after final addition) 1-bromopropane (72 mL, 0.74 mol) was added. The reaction mixture was stirred overnight and allowed to slowly warm to room temperature.

The reaction mixture was poured into a separatory funnel containing diethyl ether, and was washed with water (3×) then extracted into 1N NaOH (3×), the aqueous portion was acidified with 6N HCl to pH ~1 and the product was extracted into DCM (3×). The DCM was washed with brine (1×), dried over magnesium sulfate, and the solvent removed under vacuum to give a red oil. The oil was purified through a 6" silica gel plug, washing with 10% ethyl acetate/hexane, the solvent was then removed under vacuum to give 26.8 g of colorless oil C1.

(2) Preparation of Compound C2 (Formula (V) R$^1$=propyl)

To a mixture of C1 (26.8 g, 0.176 mol) and glyoxylic acid (50% solution in water) (17.6 mL 0.160 mol) cooled in an ice bath, added a solution of 10% NaOH (128 mL, 0.320 mol). The mixture was stirred overnight and allowed to slowly warm to room temperature. After ~15 hours 150 mL of distilled water was added to solubilize the mixture and the reaction was again stirred overnight at room temperature.

The reaction mixture was washed with ethyl acetate (4×), the aqueous portion was acidified with glacial acetic acid until pH ~3 and the product extracted into ethyl acetate (3×). The ethyl acetate was washed with brine, dried over magnesium sulfate, and the solvent was removed under vacuum to give 12 g of a white solid C2.

(3) Preparation of Compound C3 (Formula (IIb) R$^1$ and R$^4$=propyl)

PPTS (0.47 g, 1.87 mmol) was added to a solution of C2 (3.27 g, 1.44 mmol) dissolved in an excess of 1-propanol (90 mL). The solution was heated at 50 ° C. overnight.

The volume of 1-propanol was reduced under vacuum, diluted with ethyl acetate and washed with 1N HCl (3×), saturated sodium bicarbonate solution (3×), and brine (1×), and dried over magnesium sulfate. The solvent was removed under vacuum and the mixture was purified by column chromatography to give 1.7 g of colorless oil C3.

(4) Preparation of Compound C4 (Formula (III) $R^1$ and $R^4$=propyl, $R^2$ and $R^3$=ethyl)

Cesium carbonate (10 g, 30.7 mmol) was added to a solution of C3 (1.70 g, 6.36 mmol) dissolved in acetone (100 mL). After stirring for 10 minutes, 2-chloro-N,N-diethylacetamide (0.95 mL, 6.91 mmol) was added and the reaction mixture was heated at 60° C. overnight.

When the reaction was complete, the cesium carbonate was filtered off and the solvent was removed under vacuum, the mixture was purified by column chromatography to give 0.82 g of colorless oil C4.

(5) Preparation of Compound C5

To a solution of C4 (0.512 g, 1.40 mmol) dissolved in DCM (50 mL) and pyridine (0.35 mL, 4.33 mmol) and cooled in an ice bath, added acetyl bromide (0.21 mL, 2.84 mmol). The reaction mixture was stirred overnight and allowed to slowly warm to room temperature.

The mixture was poured into diethyl ether and washed with 1N HCl (3×), saturated sodium bicarbonate (3×), distilled water (1×), and brine (1×), then dried over magnesium sulfate and the solvent removed under vacuum to give 0.517 g of pink oil C5.

(6) Synthesis of Compound 4

To a solution of C5 (0.167 g, 0.394 mmol) in 1-propanol (25 mL), added 10% Pd/C (20 mg) wet with 1-propanol, and treated under hydrogen at 28 psi. After 1 hour the Pd/C was removed and replaced with another portion of 10% Pd/C (20 mg) wet with 1-propanol, and was again treated under hydrogen at 28 psi for 3hours. Pd/C was removed by filtration and the solvent removed under vacuum, the mixture was then purified by column chromatography to give 90 mg of colorless oil 4.

Alternatively, compound 4 may be prepared as in the following example.

Example 4B

Compound 4: [4-[(N,N-Diethylcarbamoyl) methoxy]-3-propoxyphenyl]acetic acid propyl ester (1) Preparation of Compound C1 (Formula (IV) $R^1$=propyl)

To a solution of catechol (100.1 g, 0.91 mol) dissolved in acetone (1 L) potassium carbonate (125.1 g, 0.91 mol) was slowly added with vigorous stirring; 1-bromopropane (90.0 mL, 0.92 mol) was added while heating and the mixture was refluxed overnight.

Once the reaction was cooled to room temperature and the potassium carbonate removed by filtration, the solvent was removed under vacuum. The product was then diluted with diethyl ether, washed with distilled water (4×), then extracted into 1N NaOH. The aqueous was collected and acidified to pH~1 with 6N HCl and the product extracted into diethyl ether, dried over magnesium sulfate and the solvent removed under vacuum. The product was purified through a 6" silica gel plug, washing with 10% ethyl acetate/hexane, and the solvent was removed under vacuum to give 45 g (0.30 mol, 32% yield) of off-white solid C1.

TLC (silica, 20% EtOAc/hexane) Rf 0.67; $^1$NMR (DMSO-$d_6$, 300 MHz): δ 0.90 (t, 3H), 1.64 (q, 2H), 3.80 (t, 2H), 6.61–6.81 (m, 4H), 8.70 (s, 1H).

(2) Preparation of Compound C2 (Formula (V) $R^1$=propyl)

To a mixture of C1 (100 g, 0.657 mol) and glyoxylic acid (50% solution in water) (67 mL, 0.648 mol) in 1 L of distilled water cooled in an ice bath, a solution of 10% NaOH (52 g NaOH in 500 ml deionized water, 1.30 mol) was slowly added via addition funnel. The mixture was stirred overnight while slowly warming to room temperature.

The reaction mixture was washed with ethyl acetate (4×), the aqueous portion was collected and acidified with 6N HCl until pH~3, and the product then extracted into ethyl acetate (3×). The ethyl acetate was washed with brine, dried over magnesium sulfate, and the solvent was removed under vacuum to give 70 g (0.31 mol, 47% yield) of a light pink solid C2.

$^1$H NMR (DMSO-$d_6$, 300 MHz): δ 0.90 (t, 3H), 1.64 (q, 2H), 3.79 (t, 2H), 4.79 (s, 1H), 5.58 (bs, 1H), 6.63–6.71 (m, 2 H), 6.85 (s, 1H), 8.77 (s, 1H), 12.3 (bs, 1H).

(3) Preparation of Compound C3 (Formula (IIb) $R^1$ and $R^4$=propyl)

To a solution of C2 (70 g, 0.289 mol) dissolved in an excess of 1-propanol (550 mL) PPTS (7.5 g, 29.8 mmol) was added and heated at 50° C. overnight.

The volume of 1-propanol was reduced under vacuum, then diluted with ethyl acetate and washed with 1N HCl (3×), saturated sodium bicarbonate solution (3×), and brine (1×), then dried over magnesium sulfate. The solvent was removed under vacuum and the mixture was then purified by column chromatography to give 55 g (0.20 mol, 71% yield) of an off-white solid C3.

TLC (silica, 50% EtOAc/hexane) Rf 0.56; $^1$H NMR (DMSO-$d_6$, 300 MHz): δ 0.69 (t, 3H), 0.89 (t, 3H), 1.43 (q, 2H), 1.64 (q, 2H), 3.79 (t, 2H), 3.89 (t, 2H), 4.89 (d, 1H), 5.76 (d, 1H), 6.63–6.69 (m, 2H), 6.84 (s, 1H), 8.80 (s, 1H).

(4) Preparation of Compound C4 (Formula (III) $R^1$ and $R^4$=propyl, $R^2$ and $R^3$=ethyl)

Potassium carbonate (95 g, 0.69 mol) was slowly added to a solution of C3 (85 g, 0.32 mol) dissolved in acetone (500 mL). The mixture was then heated to 60° C., after stirring for 1 hour 2-chloro-N,N-diethylacetamide (43.5 mL, 0.32 mol) was added and the reaction mixture was heated at 60° C. for 48 hours.

When the reaction was complete the potassium carbonate was removed by filtration and the solvent was removed under vacuum, the mixture was purified by column chromatography to give 50 g (0.13 mol, 46% yield) of colorless oil C4.

TLC (silica, 50% EtOAc/hexane) Rf 0.18; $^1$H NMR (DMSO-$d_6$, 300 MHz): δ 0.70 (t, 3H), 0.87–0.96 (m, 6H), 1.03–1.09 (m, 3H), 1.44 (q, 2H), 1.64 (q, 2H), 3.17–3.26 (m, 4H), 3.82 (t, 2H), 3.88 (t, 2H), 4.66 (s, 2H), 4.95 (d, 1H), 5.86 (d, 1H), 6.71 (d, 1H), 6.78 (d, 1H), 6.92 (s, 1H).

(5) Preparation of Compound C5

To a solution of C4 (50 g, 0.13 mol) dissolved in DCM (600 ml) and pyridine (30 ml, 0.37 mol) and cooled in an ice bath, added acetyl bromide (20 ml, 0.27 mol). The reaction mixture was stirred overnight while slowly warming to room temperature.

The solvent was reduced under vacuum then diluted with diethyl ether and washed with 1N HCl (5×), saturated sodium bicarbonate (4×), and brine (1×), then dried over magnesium sulfate. The solvent was removed under vacuum to give a yellow oil, which was then purified by column chromatography to give 50 g (0.12 mol, 91% yield) of a yellow oil C5.

TLC (silica, 50% EtOAc/hexane) Rf 0.31; $^1$H NMR (DMSO-$d_6$, 300 MHz): δ 0.70 (t, 3H), 0.87–0.96 (m, 6H), 1.03–1.09 (m, 3H), 1.44 (q, 2H), 1.64 (q, 2H), 2.02 (s, 3H), 3.17–3.26 (m, 4H), 3.84 (m, 2H), 3.95 (m, 2H), 4.71 (s, 2H), 5.73 (s, 1H), 6.76 (d, 1H), 6.90 (d, 1H), 6.99 (s, 1H).

(6) Synthesis of Compound 4

To a solution of C5 (50 g, 0.12 mol) in 1-propanol (200 mL) added 10% Pd/C (5 g) wet with 1-propanol, and treated under hydrogen at 32 psi for 48 hours with shaking. The Pd/C was removed and replaced with another portion of 10% Pd/C (2 g) wet with 1-propanol, and was again treated under hydrogen at 30 psi for 4 hours with shaking. Pd/C was removed by filtration through a millipore filter and the solvent was removed under vacuum, the product was then purified by column chromatography to give 38 g (0.10 mol, 87% yield) of colorless oil 4.

TLC (silica, 50% EtOAc/hexane) Rf 0.41; $^1$H NMR (DMSO-$d_6$, 300 MHz): δ 0.78 (t, 3H), 0.86–0.96 (m, 6H), 1.06 (t, 3H), 1.49 (q, 2H), 1.64 (q, 2H), 3.17–3.26 (m, 4H), 3.48 (s, 2H), 3.82 (t, 2H), 3.90 (t, 2H), 4.64 (s, 2H), 6.65–6.79 (m, 2H), 6.80 (s, 1H). HPLC (RP, 10–70% acetonitrile/water, 6 minute run, 214 nm) retention time 4.75 min, 100% purity by HPLC.

Example 5

Compound 5: [4-[(N,N-Dipropylcarbamoyl)methoxy]-3-ethoxyphenyl]acetic acid ethyl ester Using the procedure of Example 2, substituting 2-chloro-N,N-dipropylacetamide for 2-chloro-N,N-diethylacetamide, compound 5 was prepared. (54% yield)

$^1$H NMR (DMSO-$d_6$, 300 MHz): δ 0.69–0.80 (m, 6H), 1.09 (t, 3H), 1.24 (t, 3H), 1.37–1.47 (m, 4H), 3.09–3.17 (m, 4H), 3.46 (s, 2H), 3.90–4.02 (m, 4H), 4.66 (s, 2H), 6.65 (m, 2H), 6.78 (s, 1H). HPLC (RP, 30–90% acetonitrile/water, 6 min run, 214 nm detection) retention time 3.20 min., 97% purity by HPLC.

Example 6

Compound 6: [4-[(N,N-Dipropylcarbamoyl)methoxy]-3-ethoxyphenyl]acetic acid propyl ester Using the procedure of Example 1, substituting 2-chloro-N,N-dipropylacetamide for 2-chloro-N,N-diethylacetamide, compound 6 was prepared. (51% yield)

$^1$H NMR (DMSO-$d_6$, 300 MHz): δ 0.81–0.91 (m, 9H), 1.36 (t, 3H), 1.46–1.66 (m, 6H), 3.20–3.29 (m, 4H), 3.60 (s, 2H), 3.99–4.07 (m, 4H), 4.78 (s, 2H), 6.77 (m, 2H), 6.91 (s, 1H). HPLC (RP, 30–90% acetonitrile/water, 6 min run, 214 nm detection) retention time 3.57 min., 100% purity by HPLC.

Example 7

Compound 7: [4-[(N-Ethyl-N-methylcarbamoyl)methoxy]-3-ethoxyphenyl]acetic acid propyl ester Using the procedure of Example 1, substituting 2-chloro-N-ethyl-N-methylacetamide for 2-chloro-N,N-diethylacetamide, compound 7 was prepared. (88% yield)

$^1$H NMR (DMSO-$d_6$, 300 MHz): δ 0.89 (t, 3H), 1.28 (dt, 3H), 1.36 (t, 3H), 1.60 (q, 2H), 2.92 (d, 3H), 3.35 (m, 2H), 3.60 (s, 2H), 3.99–4.07 (m, 4H), 4.77(s, 2H), 6.79 (m, 2H), 6.91 (s, 1H). HPLC (RP, 30–90% acetonitrile/water, 6 min run, 214 nm detection) retention time 2.45 min., 99% purity by HPLC.

Example 8

Compound 8: [4-[(N-Ethyl-N-propylcarbamoyl)methoxy]-3-ethoxyphenyl]acetic acid ethyl ester Using the procedure of Example 2, substituting 2-chloro-N-ethyl-N-propylacetamide for 2-chloro-N,N-diethylacetamide, compound 8 was prepared. (64% yield)

$^1$H NMR (DMSO-$d_6$, 300 MHz): δ 0.88 (m, 3H), 1.05 (t, 15H), 1.21 (m, 4.5H), 1.36 (t, 3H), 1.47–1.65 (m, 2H), 3.21–3.41 (m, 4H), 3.59 (s, 2H), 4.00–4.14 (m, 4H), 4.77 (d, 2H), 6.77 (m, 2H), 6.90 (s, 1H). HPLC (RP, 30–90% acetonitrile/water, 6 min run, 214 nm detection) retention time 2.81 min., 95% purity by HPLC.

Example 9

Compound 9: [4-[(N-Ethyl-N-propylcarbamoyl)methoxy]-3-ethoxyphenyl]acetic acid propyl ester Using the procedure of Example 1, substituting 2-chloro-N-ethyl-N-propylacetamide for 2-chloro-N,N-diethylacetamide, compound 9 was prepared. (92% yield)

$^1$H NMR (DMSO-$d_6$, 300 MHz): δ 0.89 (m, 6H), 1.12 (dt, 3H), 1.36 (t, 3H), 1.47–0.167 (m, 4H), 3.21–3.39 (m, 4H), 3.60 (s, 2H), 4.77 (d, 2H), 6.79 (m, 2H), 6.91 (s, 1H). HPLC (RP, 30–90% acetonitrile/water, 6 min run, 214 nm detection) retention time 2.95 min., 100% purity by HPLC.

Example 10

Compound 10: [4-[(N,N-Dimethylcarbamoyl)methoxy]-3-propoxyphenyl]acetic acid propyl ester (1) Preparation of 2-[4-[(N,N-Dimethylcarbamoyl)methoxyl]-3-propoxyphenyl]-2-hydroxyacetic Acid Propyl Ester (10-D)

Using the procedure of Example 4B sub-part (4) with the reactants compound C (2.49 g, 9.28 mmol), acetone (60 mL), potassium carbonate (2.55 g, 18.5 mmol), and N,N-dimethylacetamide (1.42 g, 11.5 mmol), compound 10-D, was prepared (1.4 g)

TLC (silica, 50% EtOAc/hexane) Rf 0.11; $^1$H NMR (DMSO-$d_6$, 300 MHz): δ 0.71(t, 3H), 0.89 (t, 3H), 1.44 (q, 2H), 1.65 (q, 2H), 2.75 (s, 3H), 2.91(s, 3H), 3.80–3.91 (m, 4H), 4.69 (s, 2H), 4.95 (d, 1H), 5.86 (d, 1H), 6.72 (d, 1H), 6.77 (d, 1H), 6.91 (s, 1H).

(2) Preparation of 2-[4-[(N,N-Dimethylcarbamoyl)methoxy]-3-propoxyphenyl]-2-acetoxyacetic Acid Propyl Ester (10-E)

Using the procedure of Example 4B sub-part (5) with the reactants compound 10-D (1.4 g, 3.96 mmol), DCM (100 mL), pyridine (1.0 mL, 12.4 mmol), and acetyl bromide (0.55 mL, 7.44 mmol), compound 10-E, was prepared (1.4 g)

TLC (silica, 50% EtOAc/hexane) Rf 0.20; $^1$H NMR (DMSO-$d_6$, 300 MHz): δ 0.71(t, 3H), 0.89 (t, 3H), 1.44 (q, 2H), 1.65 (q, 2H), 2.03 (s, 3H), 2.75 (s, 3H), 2.91(s, 3H), 3.84 (t, 2H), 3.95 (m, 2H), 4.74 (s, 2H), 4.95 (d, 1H), 5.68 (s, 1H), 6.76 (d, 1H) 6.83 (d, 1H), 6.95 (s, 1H).

(3) Synthesis of Compound 10

Treating compound 10-E with hydrogen according to the process of Example 4B sub-part (6) compound 10 was prepared as a white solid (0.80 g, 2.37 mmol).

TLC (silica, 50% EtOAc/hexane) Rf 0.17; $^1$H NMR (DMSO-$d_6$, 300 MHz): δ 0.71(t, 3H), 0.89 (t, 3H), 1.44 (q, 2H), 1.65 (q, 2H), 2.75 (s, 3H), 2.91(s, 3H), 3.48 (s, 2H), 3.84 (t, 2H), 3.90 (t, 2H), 4.67 (s, 2H), 6.64 (d, 1H), 6.70 (d, 1H), 6.79 (s, 1H). HPLC (RP, 10–70% acetonitrile/water, 6 minute run, 214 nm) retention time 4.23 min, 99.2% purity by HPLC.

Example 11

Compound 11: [4-[(N-Ethyl-N-propylcarbamoyl)methoxy]-3-propoxyphenyl]acetic acid propyl ester (1) Preparation of 2-[4-[(N-Ethyl-N-propylcarbamoylmethoxy]-3-propoxyphenyl]-2-hydroxyacetic acid propyl ester (11-D)

Using the procedure of Example 4B sub-part (4) with the reactants compound C (2.43 g, 9.06 mmol), acetone (60 mL), potassium carbonate (2.50 g, 18.1 mmol), and 2-chloro-N-ethyl-N-proplyacetamide (1.94 g, 11.9 mmol) compound 11-D, was prepared (1.75 g)

TLC (silica, 50% EtOAc/hexane) Rf 0.28; $^1$H NMR (DMSO-d$_6$, 300 MHz): δ 0.67–0.79 (m, 6H), 0.87–0.99 (m, 3H), 1.00–1.07 (m, 3H), 1.40–1.47 (m, 4H), 1.65 (q, 2H), 3.11–3.31 (m, 4H), 3.82 (t, 2H), 3.88 (t, 2H), 4.66 (d, 2H), 4.94 (d, 1H), 5.85 (d, 1H), 6.74 (d, 1H), 6.77 (d, 1H), 6.92 (s, 1H)

(2) Preparation of 2-[4-[(N-Ethyl-N-propylcarbamoyl) methoxy]-3-propoxyphenyl]-2-acetoxyacetic acid propyl ester (11-E)

Using the procedure of Example 4B sub-part (5) with the reactants compound 11-D (1.70 g, 4.29 mmol), DCM (100 mL), pyridine (1.0 mL, 12.4 mmol), and acetyl bromide (0.60 mL, 4.77 mmol), compound 11-E, was prepared (2.0 g)

TLC (silica, 50% EtOAc/hexane) Rf 0.49; $^1$H NMR (DMSO-d$_6$, 300 MHz): δ 0.67–0.79 (m, 6H), 0.87–0.92 (m, 3H), 1.00–1.07 (m, 3H), 1.43–1.46 (m, 4H), 1.65 (q, 2H), 2.03 (s, 3H), 3.11–3.31 (m, 4H), 3.83 (t, 2H), 3.95 (t, 2H), 4.72 (d, 2H), 5.72 (d, 1H), 6.74 (d, 1H), 6.77 (d, 1H), 6.92 (s, 1H).

(3) Synthesis of Compound 11

Treating compound 11-E with hydrogen according to the process of Example 4B sub-part (6) compound 11 was prepared as a colorless oil (0.95 g, 2.50 mmol).

TLC (silica, 50% EtOAc/hexane) Rf 0.49; $^1$H NMR (DMSO-d$_6$, 300 MHz): δ 0.70–0.80 (m, 6H), 0.87–0.95 (m, 4.5H), 1.05 (t, 1.5H), 1.45–1.52 (m, 4H), 1.52–1.65 (m, 2H), 3.11–3.27 (m, 4H), 3.48 (s, 2H), 3.82 (t, 2H), 3.95 (t, 2H), 4.64 (d, 2H), 6.64–6.67 (q, 2H), 6.79 (s, 1H). HPLC (RP, 10–70% acetonitrile/water, 6 minute run, 214 nm) retention time 5.26 min, 100% purity by HPLC.

Example 12

Compound 12: [4-[(N,N-Dipropylcarbamoyl) methoxy]-3-propoxyphenyl]acetic acid propyl ester (1) Preparation of 2-[4-[(N,N-Dipropylcarbamoyl) methoxy]-3-propoxyphenyl]-2-hydroxyacetic acid propyl ester (12-D)

Using the procedure of Example 4B sub-part (4) with the reactants compound C (2.27 g, 8.46 mmol), acetone (60 mL), potassium carbonate (2.50 g, 18.1 mmol), and 2-chloro-N,N-diproplyacetamide (1.65 g, 9.29 mmol), compound 12-D, was prepared (1.0 g)

TLC (silica, 50% EtOAc/hexane) Rf 0.36; $^1$H NMR (DMSO-d$_6$, 300 MHz): δ 0.67–0.79 (m, 6H), 0.87–0.92 (m, 3H), 1.43–1.46 (m, 4H), 1.65 (q, 2H), 2.03 (s, 3H), 3.11–3.31 (m, 4H), 3.81 (t, 2H), 3.89 (t, 2H), 4.67 (s, 2H), 4.94 (d, 1H), 5.86 (d, 1H), 6.71 (d, 1H), 6.78 (d, 1H), 6.91 (s, 1H).

(2) Preparation of 2-[4-[(N,N-Dipropylcarbamoyl) methoxy]-3-propoxyphenyl]-2-acetoxyacetic acid propyl ester (12-E)

Using the procedure of Example 4B sub-part (5) with the reactants compound 12-D (1.70 g, 4.29 mmol), DCM (100 mL), pyridine (1.0 mL, 12.4 mmol), and acetyl bromide (0.60 mL, 4.77 mmol), compound 12-E, was prepared (1.0 g)

TLC (silica, 50% EtOAc/hexane) Rf 0.57; $^1$H NMR (DMSO-d$_6$, 300 MHz): δ 0.67–0.79 (m, 6H), 0.90 (t, 3H), 1.43–1.48 (m, 4H), 1.65 (q, 2H), 2.03 (s, 3H), 3.11–3.31 (m, 4H), 3.83 (t, 2H), 4.73 (s, 2H), 5.72 (d, 1H), 6.74 (d, 1H), 6.85 (d, 1H), 6.96 (s, 1H)

(3) Synthesis of Compound 12

Treating compound 12-E with hydrogen according to the process of Example 4B sub-part (6) compound 12 was prepared as a colorless oil (0.80 g, 2.03 mmol)

TLC (silica, 50% EtOAc/hexane) Rf 0.63; $^1$H NMR (DMSO-d$_6$, 300 MHz): δ 0.69–0.80 (m, 9H), 0.89 (t, 3H), 1.36–1.51 (m, 2H), 1.64 (q, 2H), 3.08–3.17 (m, 4H), 3.48 (s, 2H), 3.81 (t, 2H), 3.89 (t, 2H), 4.65 (s, 2H), 6.64–6.69 (m, 2H), 6.79 (s, 1H). HPLC (RP, 10–70% acetonitrile/water, 6 minute run, 214 nm) retention time 5.45 min, 100% purity by HPLC.

Example 13

Compound 13: [4-[(N-Ethyl-N-methylcarbamoyl) methoxy]-3-propoxyphenyl]acetic acid propyl ester (1) Preparation of 2-[4-[(N-Ethyl-N-methylcarbamoyl) methoxy]-3-propoxyphenyl]-2-hydroxyacetic acid propyl ester (13-D)

Using the procedure of Example 4B sub-part (4) with the reactants compound C (2.26 g, 8.42 mmol), acetone (60 mL), potassium carbonate (2.50 g, 18.1 mmol), and 2-chloro-N-ethyl-N-methylacetamide (1.26 g, 9.29 mmol) compound 13-D, was prepared (1.6 g)

TLC (silica, 50% EtOAc/hexane) Rf 0.16; $^1$NMR (DMSO-d$_6$, 300 MHz): δ 0.71 (t, 3H), 0.91 (q, 4.5H), 1.06 (t, 1.5H), 1.45 (q, 2H), 1.65 (q, 2H), 2.80 (d, 3H), 3.20–3.28 (m, 2H), 3.84 (t, 2H), 3.96 (m, 2H), 4.73 (s, 2H), 4.95 (d, 1H) 5.73 (d, 1H), 6.79 (d, 1H), 6.85 (d, 1H), 6.96 (s, 1H).

(2) Preparation of 2-[4-[(N-ethyl-N-methylcarbamoyl) methoxy]-3-propoxyphenyl]-2-acetoxyacetic acid propyl ester (13-E)

Using the procedure of Example 4B sub-part (5) with the reactants compound 13-D (1.60 g, 4.35 mmol), DCM (100 mL), pyridine (1.0 mL, 12.4 mmol), and acetyl bromide (0.60 mL, 4.77 mmol), compound 13-E, was prepared (1.9 g)

TLC (silica, 50% EtOAc/hexane) Rf 0.25; $^1$H NMR (DMSO-d$_6$, 300 MHz): δ 0.71 (t, 3H), 0.91 (q, 4.5H), 1.06 (t, 1.5H), 1.45 (q, 2H), 1.65 (q, 2H), 2.04 (s, 3H), 2.80 (d, 3H), 3.20–3.28 (m, 2H), 3.84 (t, 2H), 3.96 (m, 2H), 4.73 (s, 2H), 5.73 (s, 1H), 6.79 (d, 1H), 6.85 (d, 1H), 6.96 (s, 1H).

(3) Synthesis of Compound 13

Treating compound 13-E with hydrogen according to the process of Example 4B sub-part (6), compound 13 was prepared as a colorless oil (1.5 g, 4.27 mmol).

TLC (silica, 50% EtOAc/hexane) Rf 0.28; $^1$H NMR (DMSO-d$_6$, 300 MHz): δ 0.78 (t, 3H), 0.90 (m, 4.5H), 1.05 (t, 1.5H), 1.48 (q, 2H), 1.64 (q, 2H), 2.80 (d, 3H), 3.20–3.28 (m, 4H), 3.48 (s, 2H), 3.82 (t, 2H), 3.89 (t, 2H), 4.65 (s, 2H), 6.65–6.69 (m, 2H), 6.79 (s, 1H). HPLC (RP, 10–70% acetonitrile/water, 6 minute run, 214 nm) retention time 4.47 min, 99% purity by HPLC.

Example 14

Compound 14: [4-[(N-Ethyl-N-propylcarbamoyl) methoxy]-3-propoxyphenyl]acetic acid ethyl ester Compound 11 (0.201 g, 0.510 mmol) was saponified by dissolving in (1:1) MeOH:deionized water (10 mL). While the mixture was immersed in an ice bath, 0.1N NaOH (5.1 mL, 0.51 mmol) was added and the mixture was stirred overnight, diluted with deionized water and washed with DCM. The aqueous portion was acidified with 1N HCl, and the product extracted into DCM, and dried over magnesium sulfate. Solvent was removed under vacuum.

The acid product was redissolved in ethanol (20 mL), sulphuric acid (2 drops) was added and the mixture was heated to 110° C. overnight. Solvent was removed under vacuum and the product was then purified by column chromatography, to give compound 14 as a colorless oil (170 mg, 0.465 mmol).

TLC (silica, 50% EtOAc/hexane) Rf 0.59; $^1$H NMR (CDCl$_3$, 300 MHz): δ 0.82 (q, 3H), 0.94–1.20 (m, 9H), 1.52 (m, 2H), 1.74 (m, 2H), 3.22 (d, 2H), 3.34 (q, 2H), 3.45 (s, 2H), 3.89 (t, 2H), 4.07 (q, 2H), 4.63 (s, 2H), 6.68 (d, 1H), 6.76 (s, 12H), 6.81 (d, 1H). HPLC (RP, 10–70% acetonitrile/water, 6 minute run, 214 nm) retention time 4.88 min, 95% purity by HPLC.

Example 15

Comparison Compound Propanidid: [4-[(N,N-diethylcarbamoyl)methoxy]-3-methoxyphenyl]acetic acid propyl ester (1) Preparation of 3-methoxy-4-hydroxyphenylacetic acid propyl ester (15-A)

4-Hydroxy-3-methoxyphenethyl alcohol (Sigma-Aldrich) was dissolved in anhydrous 1-propanol. To this solution ~5 drops of concentrated sulphuric acid were added and the solution was heated at 100° C. for 3–5 hours in a pressure tube. When the reaction was complete, the 1-propanol was removed under reduced pressure, the resulting oil was diluted with ethyl acetate and washed with saturated sodium bicarbonate solution, distilled water, and then brine. The solution was dried over magnesium sulfate and filtered and the solvent was removed under reduced pressure, giving 15-A as a red oil in almost quantitative yield.

$^1$H NMR (DMSO, 300 MHz) δ 0.77 (3H, t, CH$_3$), 1.47 (2H, q, CH$_2$), 3.44 (2H, s, ArCH$_2$CO), 3.65 (3H, s, OCH$_3$), 3.89 (2H, t, OCH$_2$), 6.60 (2H, m, ArH), 6.73 (1H, s, ArH), 8.79 (1H, s, ArOH)

(2) Preparation of [4-[(N,N-diethylcarbamoyl)methoxy]-3-methoxyphenyl]acetic Acid Propyl Ester 3-Methoxy-4-hydroxyphenylacetic acid propyl ester (15-A) was dissolved in acetone. To the solution, 2 equivalents of K$_2$CO$_3$ were added, followed by 1.2 equivalent of 2-chloro-N,N-diethylacetamide. Under vigorous stirring, the suspension was warmed to reflux (60° C.) for ~15 hours. After cooling to room temperature the reaction mixture was filtered and the remaining solvent removed under reduced pressure, giving a 95% yield of a dark yellow oil. The oily product was purified by silica column chromatography to produce the title compound.

$^1$H NMR (DMSO, 300 MHz) δ 0.78 (3H, t, CH$_3$), 0.94 (3H, t, CH$_3$), 1.05 (3H, t, CH$_3$), 1.49 (2H, q, CH$_2$), 3.20 (4H, m, N-ethyl CH$_2$), 3.49 (2H, s, ArCH$_2$CO), 3.66(3H, s, OCH$_3$), 3.90 (2H, t, OCH$_2$), 4.63 (2H, s, OCH$_2$CO), 6.72 (2H, m, ArH), 6.80 (1H, s, ArH)

Example 16

The following illustrates representative pharmaceutical dosage forms, containing a compound of the invention "compound X"

|  | wt. % |
|---|---|
| (i) Injection 1 | |
| 'Compound X' | 2.0 |
| soy bean oil | 10.0 |
| egg phosphatide | 1.2 |
| glycerol | 2.25 |
| disodium edetate dihydrate | 0.0055 |
| sodium hydroxide | q.s. |
| water for injection | to 100 |
| (ii) Injection 2 | |
| 'Compound X' | 1.0 |
| soy bean oil | 5.0 |
| fractionated coconut oil | 5.0 |
| egg phosphatide | 1.2 |
| glycerol | 2.25 |
| disodium edetate dihydrate | 0.0055 |
| sodium hydroxide | q.s. |
| water for injection | to 100 |
| (iii) Injection 3 | |
| 'Compound X' | 1.0% w/v |
| N-methylpyrrolidinone | 30% w/v |
| propylene glycol | 40% w/v |
| water for injection | |
| (iv) Injection 4 | |
| 'Compound X' | 2.0% w/v |
| N-methylpyrrolidinone | 30% w/v |
| propylene glycol | 40% w/v |
| water for injection | |
| (v) Injection 5 | |
| 'Compound X' | 1.0 |
| soy bean oil | 1.0–3.0 |
| lecithin | 1.2 |
| glycerol | 2.25 |
| sodium hydroxide | q.s. |
| water for injection | to 100 |
| (vi) Injection 6 | |
| 'Compound X' | 1.0% w/v |
| soybean oil | 10.0% w/v |
| safflower oil | 10.0% w/v |
| egg phosphatids | 1.2% w/v |
| glycerol | 2.5% w/v |
| sodium hydroxide | q.s. |
| water for injection | |
| (vii) Injection 7 | |
| 'Compound X' | 1.0% w/v |
| soybean oil | 10.0% w/v |
| egg phosphatides | 1.2% w/v |
| glycerol | 2.5% w/v |
| sodium hydroxide | q.s. |
| water for injection | |
| (viii) Injection 8 | |
| 'Compound X' | 1.0% w/v |
| soybean oil | 30% w/v |
| phosphatidylcholine from egg yolk | 1.2% w/v |
| glycerol | 1.67% w/v |
| sodium hydroxide | q.s. |
| water for injection | |
| (ix) Injection 9 | |
| 'Compound X' | 4.0% w/v |
| soybean oil | 20% w/v |
| lecithin | 2.4% w/v |

-continued

| | wt. % |
|---|---|
| glycerol | 2.5% w/v |
| oleic acid | 0.03% w/v |
| 0.1 N sodium hydroxide | q.s. to pH 8 |
| water for injection | |
| (x) Injection 10 | |
| | |
| 'Compound X' | 10.0% w/v |
| caprylic/capric triglyceride | 10.0% w/v |
| egg phosphatides | 1.2% w/v |
| glycerol | 2.5% w/v |
| sodium hydroxide | q.s. |
| water for injection | |
| (xi) Injection 11 | |
| | |
| 'Compound X' | 5.0% w/v |
| caprylic/capric triglyceride | 15.0% w/v |
| egg phosphatides | 1.2% w/v |
| glycerol | 2.5% w/v |
| sodium hydroxide | q.s. |
| water for injection | |
| (xii) Injection 12 | |
| | |
| 'Compound X' | 10% w/v |
| Miglyol ® 810 | 5.0–10.0% w/v |
| egg yolk phosphatides | 0.5–1.0% w/v |
| DMPG | 0.1% w/v |
| glycerol | 2.25% w/v |
| sodium hydroxide | q.s. |
| water for injection | |

The above formulations may be obtained by conventional procedures well known in the pharmaceutical art. For example, a formulation of compound 1 according to Injection 9 was prepared by the following procedure.

A mixture of L-α-phosphatidylcholine 60% (lecithin) (2.40 g), glycerol (98%) (2.50 g), (both from Sigma-Aldrich), oleic acid (99%) (0.03 g) (Fluka-Sigma-Aldrich, Buchs, Switzerland) and deionized water (71.1 g) was heated at 60° C. until fully dissolved giving an opaque solution. The pH was adjusted to pH 8 while the solution was still warm by addition of 0.1 N NaOH. A mixture of compound 1 (4.0 g) and soybean oil (Sigma-Aldrich) (20.0 g) was heated to 60° C. until miscible and then added to the first mixture. The solution was stirred briefly at 60° C. and then transferred to a beaker and stirred with a Polytron tissue homogenizer for 5 min at maximum speed to provide a premixed solution.

A microfluidizer (Microfluidics Corp., Newton, Mass., model no. 110S) was washed with isopropanol and then deionized water. The microfluidizer were primed with a minimal amount of the premixed solution. The reservoir of the microfluidizer was filled with the premixed solution and the solution was circulated through the mixing chamber for 30 see at maximum pressure (~12000–15000 psi). The first 10 drops of microfluidized solution were collected and discarded, then all subsequent fractions were collected in a glass vial.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

wherein
$R^1$ is selected from the group consisting of $(C_2-C_6)$alkyl, $(C_2-C_6)$alkenyl, $(C_2-C_6)$alkynyl, $(C_3-C_6)$cycloalkyl $(C_1-C_6)$alkyl, $(C_3-C_6)$cycloalkyl, phenyl, and benzyl;
$R^2$ and $R^3$ are each independently selected from the group consisting of $(C_1-C_6)$alkyl, $(C_2-C_6)$alkenyl, and $(C_2-C_6)$alkynyl, or $R^2$ and $R^3$, together with the nitrogen atom to which they are attached, form a heterocyclic ring having from 5 to 7 atoms, and
$R^4$ is selected from the group consisting of $(C_1-C_6)$alkyl, $(C_2-C_6)$alkenyl, and $(C_2-C_6)$alkynyl;
provided that the sum of the number of carbon atoms in $R^1$, $R^2$, $R^3$, and $R^4$ is greater than 7.

2. The compound of claim 1, wherein $R^1$ is selected from the group consisting of $(C_2-C_6)$alkyl, $(C_2-C_6)$alkenyl, and $(C_2-C_6)$alkynyl.

3. The compound of claim 1, wherein $R^1$ is selected from the group consisting of $(C_3-C_6)$cycloalkyl, phenyl, and benzyl.

4. The compound of claim 1, wherein $R^1$ is $(C_2-C_4)$alkyl.

5. The compound of claim 4, wherein $R^1$ is ethyl or propyl.

6. The compound of claim 1, wherein $R^2$ is selected from the group consisting of $(C_1-C_4)$alkyl, $(C_2-C_4)$alkenyl, and $(C_2-C_4)$alkynyl.

7. The compound of claim 6, wherein $R^2$ is $(C_1-C_4)$alkyl.

8. The compound of claim 1, wherein $R^3$ is selected from the group consisting of $(C_1-C_4)$alkyl, $(C_2-C_4)$alkenyl, and $(C_2-C_4)$alkynyl.

9. The compound of claim 8, wherein $R^3$ is $(C_1-C_4)$alkyl.

10. The compound of claim 1, wherein $R^4$ is selected from the group consisting of $(C_1-C_4)$alkyl, $(C_2-C_4)$alkenyl, and $(C_2-C_4)$alkynyl.

11. The compound of claim 10, wherein $R^4$ is $(C_1-C_4)$ alkyl.

12. The compound of claim 1, wherein the sum of the number of carbon atoms in $R^1$, $R^2$, $R^3$, and $R^4$ ranges from 8 to 15.

13. The compound of claim 12, wherein $R^1$ is $(C_2-C_4)$ alkyl; $R^2$, $R^3$, and $R^4$ are each independently $(C_1-C_4)$alkyl; and the sum of the number of carbon atoms in $R^1$, $R^2$, $R^3$, and $R^4$ ranges from 8 to 12.

14. The compound of claim 13, wherein $R^1$ is ethyl or propyl; $R^2$, $R^3$, and $R^4$ are each independently selected from the group consisting of methyl, ethyl, and propyl; and the sum of the number of carbon atoms in $R^1$, $R^2$, $R^3$, and $R^4$ ranges from 8 to 11.

15. The compound of claim 14 wherein the sum of the number of carbon atoms in $R^1$, $R^2$, $R^3$, and $R^4$ is 9, 10, or 11.

16. The compound of claim 14, wherein $R^2$ and $R^3$ are each ethyl and $R^4$ is propyl.

17. The compound having the chemical name [4-[(N,N-diethylcarbamoyl)methoxy]-3-ethoxyphenyl]acetic acid propyl ester.

18. A pharmaceutical composition comprising a compound of any one of claims 1–16 and a pharmaceutically acceptable carrier.

19. A pharmaceutical composition comprising a compound of claim 17 and a pharmaceutically acceptable carrier.

20. The composition of claim 18 further comprising a therapeutic agent selected from the group consisting of another sedative hypnotic agent, an analgesic, and a paralytic agent.

21. The composition of claim 18 further comprising an analgesic.

22. The composition of claim 21 wherein the analgesic is an opioid.

23. A method for inducing or maintaining anesthesia or sedation in a mammal, wherein the method comprises administering to the mammal a therapeutically effective amount of a compound of any one of claims 1–16.

24. A method for inducing or maintaining anesthesia or sedation in a mammal, wherein the method comprises administering to the mammal a therapeutically effective amount of a composition of claim 18.

25. The method of claim 24 wherein the method further comprises administering to the mammal a therapeutically effective amount of a therapeutic agent selected from the group consisting of another sedative hypnotic agent, an analgesic, and a paralytic agent.

26. The compound of claim 4 wherein $R^1$ is ethyl.

27. The compound of claim 1 wherein $R^1$ is ethyl or propyl, $R^2$ is ethyl, propyl or methyl, $R^3$ is ethyl, propyl or methyl and $R^4$ is ethyl, propyl or isopropyl.

28. A method for inducing or maintaining anesthesia or sedation in a mammal, wherein the method comprises administering to the mammal a therapeutically effective amount of a compound of claim 17.

29. A method for inducing or maintaining anesthesia or sedation in a mammal, wherein the method comprises administering to the mammal a therapeutically effective amount of a composition of claim 19.

30. The method of claim 29 wherein the method further comprises administering to the mammal a therapeutically effective amount of a therapeutic agent selected from the group consisting of another sedative hypnotic agent, an analgesic, and a paralytic agent.

31. The composition of claim 19 further comprising a therapeutic agent selected from the group consisting of another sedative hypnotic agent, an analgesic, and a paralytic agent.

32. The composition of claim 19 further comprising an analgesic.

33. The composition of claim 31 wherein the analgesic is an opioid.

* * * * *